(12) United States Patent
Quistad et al.

(10) Patent No.: US 6,251,862 B1
(45) Date of Patent: Jun. 26, 2001

(54) INSECTICIDAL TOXINS FROM THE PARASITIC WASP *BRACON HEBETER*

(75) Inventors: Gary B. Quistad, Mountain View, CA (US); Douglas J. Leisy, Corvalis, OR (US)

(73) Assignee: Syngenta Participations AG, Basel (CH)

(*) Notice: Subject to any disclaimer, the term of this patent is extended or adjusted under 35 U.S.C. 154(b) by 0 days.

(21) Appl. No.: 08/655,782

(22) Filed: May 31, 1996

Related U.S. Application Data

(63) Continuation of application No. 08/288,408, filed on Aug. 10, 1994, now Pat. No. 5,554,592, which is a continuation of application No. 08/013,890, filed on Feb. 5, 1993, now abandoned, which is a continuation-in-part of application No. 07/897,192, filed on Jun. 10, 1992, now abandoned, which is a continuation-in-part of application No. 07/847,570, filed on Mar. 4, 1992, now abandoned.

(51) Int. Cl.⁷ .................................................. A61K 38/00
(52) U.S. Cl. ................. 514/12; 514/2; 530/350; 530/858; 536/23.1; 424/405; 424/538; 435/69.1
(58) Field of Search ............... 514/2, 12; 530/350, 530/858; 424/538, 405; 435/69.1; 536/23.1

(56) References Cited

U.S. PATENT DOCUMENTS 5,554,592   9/1996   Quistad et al. ............... 514/12

OTHER PUBLICATIONS

Slavnova et al., Doklady Akademii Nauk SSR, 297(2):492–494 (1987).

Visser et al., Comp. Biochem. Physiol., 75B(3):523,530 (1983).

Piek et al., Comp. Biochem. Physiol., 72C:303–309 (1982).

Spanjer et al., Toxicon, 15:413–421 (1977).

Visser et al., Toxicon, 14:357,370 (1976).

Walter et al., Neuroscience 9(1):213–224 (1983).

Drenth et al., Toxicon, 12:189–192 (1974).

R. L. Beard, Toxins of Animal and Plant Origin, vol. 1 deVries et al., Eds. Gordon and Breach Science Publishers, New York, 181–190 (1971).

T. Piek, J. Insect Physiol., 12:561–568 (1966).

*Primary Examiner*—Karen Cochrane Carlson
*Assistant Examiner*—Stephen Tu
(74) *Attorney, Agent, or Firm*—J. Timothy Meigs

(57) ABSTRACT

Novel polypeptides are isolated from the venom of the parasitic wasp, *Bracon hebetor*, and are designated Brh-I to Brh-V. These polypeptides are paralytic and/or toxic to insects. The entire amino acid sequence of Brh-I and the DNA encoding it is also determined. These polypeptides may be cloned into a baculovirus, and used for insect control.

16 Claims, 7 Drawing Sheets

SEQUENCE LISTING (1) GENERAL INFORMATION:

(iii) NUMBER OF SEQUENCES: 13

(2) INFORMATION FOR SEQ ID NO: 1:

(i) SEQUENCE CHARACTERISTICS:
      (A) LENGTH: 45 amino acids
      (B) TYPE: amino acid
      (C) STRANDEDNESS: single
      (D) TOPOLOGY: linear (xi) SEQUENCE DESCRIPTION: SEQ ID NO: 1:

```
Xaa Thr Asp Phe Tyr Tyr Thr Asp Val Ile Ala Asp Gln Asp Phe Leu
1               5                   10                  15

Leu Lys Gln Lys Lys Val Phe Gln Leu Leu Tyr His Val Ser Gln Pro
                20                  25                  30

Xaa Ile Ser Asn Xaa Xaa Xaa Phe Gln Xaa Xaa Leu Lys
            35                  40                  45
```

(2) INFORMATION FOR SEQ ID NO: 2:

(i) SEQUENCE CHARACTERISTICS:
      (A) LENGTH: 28 amino acids
      (B) TYPE: amino acid
      (C) STRANDEDNESS: single
      (D) TOPOLOGY: linear (xi) SEQUENCE DESCRIPTION: SEQ ID NO: 2:

```
Xaa His Val Gln Thr Tyr Thr Ala Asp Met Asp Phe Lys His Lys Gln
1               5                   10                  15

Lys Lys Ile Tyr His Leu Phe Xaa Xaa Xaa Xaa Gln
```

```
                        20                  25

(2) INFORMATION FOR SEQ ID NO: 3:

(i) SEQUENCE CHARACTERISTICS:
        (A) LENGTH: 41 amino acids
        (B) TYPE: amino acid
        (C) STRANDEDNESS: single
        (D) TOPOLOGY: linear (xi) SEQUENCE DESCRIPTION: SEQ ID NO: 3:

Xaa Leu Phe Asp Phe Ile Val His Ala Lys Asp Ile Leu Gly Gly Ile
1               5                   10                  15

Asp Asn Leu Ala Lys Gly Ile Xaa Xaa Ala Ile Asn Lys Val Xaa Xaa
                20                  25                  30

Val Ile Xaa Lys Val Gln Xaa Gln Ala
            35                  40

(2) INFORMATION FOR SEQ ID NO: 4:

(i) SEQUENCE CHARACTERISTICS:
        (A) LENGTH: 2387 base pairs
        (B) TYPE: nucleic acid
        (C) STRANDEDNESS: double
        (D) TOPOLOGY: linear (ix) FEATURE:
        (A) NAME/KEY: CDS
        (B) LOCATION: 85..2118
        (D) OTHER INFORMATION: /codon_start= 85
            /number= 1

(ix) FEATURE:
        (A) NAME/KEY: CDS
        (B) LOCATION: 85..2118
        (D) OTHER INFORMATION: /codon_start= 85

(ix) FEATURE:
        (A) NAME/KEY: CDS
        (B) LOCATION: 85..2118

(xi) SEQUENCE DESCRIPTION: SEQ ID NO: 4:

GCAACACAAG TGTTACTTCG TTTGCCACTT CACTGTTGAA GAAAAATAAA AAATACATTT      60

TGATTATCAC TTGAATAATC TATA ATG CTG AAG AAG GTC TTT CTT TTG GCC       111
                          Met Leu Lys Lys Val Phe Leu Leu Ala
                           1               5

TCT TTG GCT ATT ATC GTG ATA AAA GCT GAT ACC GAT TTT TAT TAT ACA      159
Ser Leu Ala Ile Ile Val Ile Lys Ala Asp Thr Asp Phe Tyr Tyr Thr
 10              15                  20                  25

GAT GTG ATA GCT GAT CAA GAT TTC CTT TTA AAG CAA AAG AAA GTT TTT      207
Asp Val Ile Ala Asp Gln Asp Phe Leu Leu Lys Gln Lys Lys Val Phe
                30                  35                  40

CAA TTG TTG TAT CAT GTT TCA CAA CCA GAC ATC TCA AAT CCC GAG CTT      255
Gln Leu Leu Tyr His Val Ser Gln Pro Asp Ile Ser Asn Pro Glu Leu
            45                  50                  55

TTC CAG GAG GGA TTG GCT TAT GAC ATT GGA GCC AAT ATT GAT TCC TAT      303
Phe Gln Glu Gly Leu Ala Tyr Asp Ile Gly Ala Asn Ile Asp Ser Tyr
        60                  65                  70

TCT AAT AAG GAT GCA GTG AAT CAC TTC CTC GAG CTA TAC AAA TTC GGA      351
Ser Asn Lys Asp Ala Val Asn His Phe Leu Glu Leu Tyr Lys Phe Gly
    75                  80                  85

TTC CTT CCA AGA GGT GCA ATC TAC TCC CTC TAT TAT CCT AAA CTC TTG      399
Phe Leu Pro Arg Gly Ala Ile Tyr Ser Leu Tyr Tyr Pro Lys Leu Leu
 90                  95                  100                 105

GAC GAG ACT AAA GCC TTG TTC AAA TTG TTC TAC TAT GCC AAG GAC TTT      447
```

-continued

```
              Asp Glu Thr Lys Ala Leu Phe Lys Leu Phe Tyr Tyr Ala Lys Asp Phe
                              110                 115                 120

GAT ACT TTC TAT AAA ACT GCC CTT TGG GCG AGA AAT CGT TTG AAC GAA            495
Asp Thr Phe Tyr Lys Thr Ala Leu Trp Ala Arg Asn Arg Leu Asn Glu
            125                 130                 135

GGT GAA TTC ATA TGT GCC TTC TAT GAA GCT GTC ATC CGG CGT CCC GAC            543
Gly Glu Phe Ile Cys Ala Phe Tyr Glu Ala Val Ile Arg Arg Pro Asp
            140                 145                 150

ACA GAG TAT CTC CAG TTA CCA CCG CCT TAT GAG TTA TAT CCC TAT GCG            591
Thr Glu Tyr Leu Gln Leu Pro Pro Pro Tyr Glu Leu Tyr Pro Tyr Ala
            155                 160                 165

TTC TTC AAC AGT GAG GTA ATC GAG GCT GCA AAA AAT GCC AAA TTG TAC            639
Phe Phe Asn Ser Glu Val Ile Glu Ala Ala Lys Asn Ala Lys Leu Tyr
170                 175                 180                 185

AAT AAG CTT GTT GAA GGA AAT TCC TAC ATT ATC TAT GTC AAT TAC TCC            687
Asn Lys Leu Val Glu Gly Asn Ser Tyr Ile Ile Tyr Val Asn Tyr Ser
                190                 195                 200

GGC TGG TAC TTG AAT CGA GCT TAT GAT ACA GAG ATG AGA GTC AAC TAT            735
Gly Trp Tyr Leu Asn Arg Ala Tyr Asp Thr Glu Met Arg Val Asn Tyr
            205                 210                 215

TTC CTC GAA GAT ATC GGT TTA AAC ACC TTC TAC TTT TTC TAC CGC ATG            783
Phe Leu Glu Asp Ile Gly Leu Asn Thr Phe Tyr Phe Phe Tyr Arg Met
            220                 225                 230

GAT AAT CCA TTT TGG TTG AGC AGT GAG GAA TTT GGT TTG CAG AAA AAT            831
Asp Asn Pro Phe Trp Leu Ser Ser Glu Glu Phe Gly Leu Gln Lys Asn
235                 240                 245

TTG CGT GGT GAG GAA TTT CTC TAT GTT CAC AAA ACA CTC TTG AAT CGT            879
Leu Arg Gly Glu Glu Phe Leu Tyr Val His Lys Thr Leu Leu Asn Arg
250                 255                 260                 265

TAC AAT TTG GAA AGA TTG GCA AAT GGC TTG GAG AAA ATT GAA GAA TTC            927
Tyr Asn Leu Glu Arg Leu Ala Asn Gly Leu Glu Lys Ile Glu Glu Phe
                270                 275                 280

CTT TGG GAG GGA GAA TTT TAT CCA GGC TAT TAT CCA ACT ATG GTC TAT            975
Leu Trp Glu Gly Glu Phe Tyr Pro Gly Tyr Tyr Pro Thr Met Val Tyr
            285                 290                 295

GGC AAT GGG CTG GCT TAT CCT CAG CGT CCA GGA ATG AGT AGG ATT CCT           1023
Gly Asn Gly Leu Ala Tyr Pro Gln Arg Pro Gly Met Ser Arg Ile Pro
            300                 305                 310

CCA TAT AAG TAT CAT TAT TTA CGG TAT ATC CAC GAT ATC GAA GAT AGA           1071
Pro Tyr Lys Tyr His Tyr Leu Arg Tyr Ile His Asp Ile Glu Asp Arg
            315                 320                 325

ATT TCA ACA GCC ATT GAC TTG GGC TAT ATA ATC GAC AGC GAT GGT AGT           1119
Ile Ser Thr Ala Ile Asp Leu Gly Tyr Ile Ile Asp Ser Asp Gly Ser
330                 335                 340                 345

CAC CAC AAC ATC TCA AGT CCC GAA GGA CTT AAC CTC TTA GGT AAC ATC           1167
His His Asn Ile Ser Ser Pro Glu Gly Leu Asn Leu Leu Gly Asn Ile
                350                 355                 360

ATC GAG GGT AAT GAA GAT AGT TGC AAT AAA AAC TTT TAT CAC AGC CTC           1215
Ile Glu Gly Asn Glu Asp Ser Cys Asn Lys Asn Phe Tyr His Ser Leu
            365                 370                 375

GAT TGG TAT GGT AGA AAG GTT CTT GGT TTC AAT CTC GAG CCC AAG ACT           1263
Asp Trp Tyr Gly Arg Lys Val Leu Gly Phe Asn Leu Glu Pro Lys Thr
            380                 385                 390

CCC TAT CAA GTT ATT CCA AGT GCA CTA GAG TCA TTT TCA ACT TGC ATG           1311
Pro Tyr Gln Val Ile Pro Ser Ala Leu Glu Ser Phe Ser Thr Cys Met
            395                 400                 405

AGA GAT CCG GCT TTC TAT CGT CTC TAC AAT AGA TAT CTG TCA TAC TGG           1359
Arg Asp Pro Ala Phe Tyr Arg Leu Tyr Asn Arg Tyr Leu Ser Tyr Trp
410                 415                 420                 425
```

```
TAC AGA TTC AAA GAA ACC TTG AAG CCA TAT TCT AAG AAT GAA ATA GTC      1407
Tyr Arg Phe Lys Glu Thr Leu Lys Pro Tyr Ser Lys Asn Glu Ile Val
                430                 435                 440

TTC TCT GAT TTG AAA TTT GAA TCA ATT GCT GTT GAT AAA TTG ATC ACA      1455
Phe Ser Asp Leu Lys Phe Glu Ser Ile Ala Val Asp Lys Leu Ile Thr
            445                 450                 455

TAT TTT GAT TAT TTT GAT TCA ACA ATT AGC AAT GGT CTA CCA ATT ACA      1503
Tyr Phe Asp Tyr Phe Asp Ser Thr Ile Ser Asn Gly Leu Pro Ile Thr
        460                 465                 470

AGT AAA CAA GAT GCT GAT AAT TTA ATG ATC AAA GTT CGC CAG AGT CGT      1551
Ser Lys Gln Asp Ala Asp Asn Leu Met Ile Lys Val Arg Gln Ser Arg
    475                 480                 485

TTA AAT AAT AAA CAC TTT ACC GTA CAT TTC GCC CTA AAT TCC GAT AAA      1599
Leu Asn Asn Lys His Phe Thr Val His Phe Ala Leu Asn Ser Asp Lys
490                 495                 500                 505

GCA CAA AAA GTT GCC ATT CAG CTG TTT CTT GGA CCC AAA TAT GAT GCA      1647
Ala Gln Lys Val Ala Ile Gln Leu Phe Leu Gly Pro Lys Tyr Asp Ala
                510                 515                 520

CTT GGT AAT TTA TTG GAC TTT TCC GAG AGT TAC AAA GAC TTT TAT GAG      1695
Leu Gly Asn Leu Leu Asp Phe Ser Glu Ser Tyr Lys Asp Phe Tyr Glu
            525                 530                 535

ATT GAC TAC TGG ATT ACT GAT GTG AAT GCT GGC TTG AAT AAA CTT GAA      1743
Ile Asp Tyr Trp Ile Thr Asp Val Asn Ala Gly Leu Asn Lys Leu Glu
        540                 545                 550

CGT ACC AGT CAC GAC TTT ATC TTT TTG ATG GCC GAC CGA GAT CCA AGT      1791
Arg Thr Ser His Asp Phe Ile Phe Leu Met Ala Asp Arg Asp Pro Ser
    555                 560                 565

GAA ATT TTA TAC AAA AGA GTT TTA AAG GCC CTT GAT GGA AGT GAA AAG      1839
Glu Ile Leu Tyr Lys Arg Val Leu Lys Ala Leu Asp Gly Ser Glu Lys
570                 575                 580                 585

TTC ATG TAC AAA AAG AAT TTG TAT GGC ATT CCG GAA CGT TTA CTT CTA      1887
Phe Met Tyr Lys Lys Asn Leu Tyr Gly Ile Pro Glu Arg Leu Leu Leu
                590                 595                 600

CCA AAA GGT AAA CGT GCC GGT AGT ATT TTC CAA CTG TTT GCC TAT GTA      1935
Pro Lys Gly Lys Arg Ala Gly Ser Ile Phe Gln Leu Phe Ala Tyr Val
            605                 610                 615

AGC CCA GTT ACC CAG CCA GTC ACC TAC AAA TCA CGA GTA TTT GGA TCT      1983
Ser Pro Val Thr Gln Pro Val Thr Tyr Lys Ser Arg Val Phe Gly Ser
        620                 625                 630

TAT CAA TAC TAC ATG AAA CCA GGT GGT TTT CCA CTG GAC AGG CCA ATC      2031
Tyr Gln Tyr Tyr Met Lys Pro Gly Gly Phe Pro Leu Asp Arg Pro Ile
    635                 640                 645

TAC TAT CCC CAT TTC CAA GGG CCC AAT ATG TTC TTC AAA GAT ATT ACG      2079
Tyr Tyr Pro His Phe Gln Gly Pro Asn Met Phe Phe Lys Asp Ile Thr
650                 655                 660                 665

ATT TAC CAC AAG ACT GAT GTG GAT CCT AAT GCT ACT ACC TAATTCCAAT      2128
Ile Tyr His Lys Thr Asp Val Asp Pro Asn Ala Thr Thr
                670                 675

TTTTTTACTC TATTTTCATT TGAGATTCTT ATCAAATTCA ATGTTTGTTT GTTAATATTG    2188

TCTTTGTAGA GCTTAGAATG TTAGATTGAA AATGTTTATT TCCATGACAA TTTATTATTT    2248

GTTATTGATA TTATCAATGA ATTCTCTGTC AGTCAACCTC AGAGAATATA AAATTTTATT    2308

ACAAAAATGT CGTATTGAGC ATAAATTCAT TATTTGGGAA AAATTTTCAA ATAAAAAGCA    2368

TATTTTCCAA CAAAAAAAA                                                 2387
```

(2) INFORMATION FOR SEQ ID NO: 5:

(i) SEQUENCE CHARACTERISTICS:
        (A) LENGTH: 678 amino acids (B) TYPE: amino acid
(D) TOPOLOGY: linear (ii) MOLECULE TYPE: protein (xi) SEQUENCE DESCRIPTION: SEQ ID NO: 5:

```
Met Leu Lys Lys Val Phe Leu Leu Ala Ser Leu Ala Ile Ile Val Ile
 1               5                  10                  15

Lys Ala Asp Thr Asp Phe Tyr Thr Asp Val Ile Ala Asp Gln Asp
                20                  25                  30

Phe Leu Leu Lys Gln Lys Lys Val Phe Gln Leu Leu Tyr His Val Ser
             35                  40                  45

Gln Pro Asp Ile Ser Asn Pro Glu Leu Phe Gln Glu Gly Leu Ala Tyr
         50                  55                  60

Asp Ile Gly Ala Asn Ile Asp Ser Tyr Ser Asn Lys Asp Ala Val Asn
 65                  70                  75                  80

His Phe Leu Glu Leu Tyr Lys Phe Gly Phe Leu Pro Arg Gly Ala Ile
                 85                  90                  95

Tyr Ser Leu Tyr Tyr Pro Lys Leu Leu Asp Glu Thr Lys Ala Leu Phe
                100                 105                 110

Lys Leu Phe Tyr Tyr Ala Lys Asp Phe Asp Thr Phe Tyr Lys Thr Ala
            115                 120                 125

Leu Trp Ala Arg Asn Arg Leu Asn Glu Gly Glu Phe Ile Cys Ala Phe
    130                 135                 140

Tyr Glu Ala Val Ile Arg Arg Pro Asp Thr Glu Tyr Leu Gln Leu Pro
145                 150                 155                 160

Pro Pro Tyr Glu Leu Tyr Pro Tyr Ala Phe Phe Asn Ser Glu Val Ile
                165                 170                 175

Glu Ala Ala Lys Asn Ala Lys Leu Tyr Asn Lys Leu Val Glu Gly Asn
                180                 185                 190

Ser Tyr Ile Ile Tyr Val Asn Tyr Ser Gly Trp Tyr Leu Asn Arg Ala
        195                 200                 205

Tyr Asp Thr Glu Met Arg Val Asn Tyr Phe Leu Glu Asp Ile Gly Leu
    210                 215                 220

Asn Thr Phe Tyr Phe Phe Tyr Arg Met Asp Asn Pro Phe Trp Leu Ser
225                 230                 235                 240

Ser Glu Glu Phe Gly Leu Gln Lys Asn Leu Arg Gly Glu Glu Phe Leu
                245                 250                 255

Tyr Val His Lys Thr Leu Leu Asn Arg Tyr Asn Leu Glu Arg Leu Ala
            260                 265                 270

Asn Gly Leu Glu Lys Ile Glu Glu Phe Leu Trp Glu Gly Glu Phe Tyr
    275                 280                 285

Pro Gly Tyr Tyr Pro Thr Met Val Tyr Gly Asn Gly Leu Ala Tyr Pro
290                 295                 300

Gln Arg Pro Gly Met Ser Arg Ile Pro Pro Tyr Lys Tyr His Tyr Leu
305                 310                 315                 320

Arg Tyr Ile His Asp Ile Glu Asp Arg Ile Ser Thr Ala Ile Asp Leu
                325                 330                 335

Gly Tyr Ile Ile Asp Ser Asp Gly Ser His His Asn Ile Ser Ser Pro
            340                 345                 350

Glu Gly Leu Asn Leu Leu Gly Asn Ile Ile Glu Gly Asn Glu Asp Ser
        355                 360                 365

Cys Asn Lys Asn Phe Tyr His Ser Leu Asp Trp Tyr Gly Arg Lys Val
370                 375                 380
```

```
Leu Gly Phe Asn Leu Glu Pro Lys Thr Pro Tyr Gln Val Ile Pro Ser
385                 390                 395                 400

Ala Leu Glu Ser Phe Ser Thr Cys Met Arg Asp Pro Ala Phe Tyr Arg
                405                 410                 415

Leu Tyr Asn Arg Tyr Leu Ser Tyr Trp Tyr Arg Phe Lys Glu Thr Leu
            420                 425                 430

Lys Pro Tyr Ser Lys Asn Glu Ile Val Phe Ser Asp Leu Lys Phe Glu
        435                 440                 445

Ser Ile Ala Val Asp Lys Leu Ile Thr Tyr Phe Asp Tyr Phe Asp Ser
    450                 455                 460

Thr Ile Ser Asn Gly Leu Pro Ile Thr Ser Lys Gln Asp Ala Asp Asn
465                 470                 475                 480

Leu Met Ile Lys Val Arg Gln Ser Arg Leu Asn Asn Lys His Phe Thr
                485                 490                 495

Val His Phe Ala Leu Asn Ser Asp Lys Ala Gln Lys Val Ala Ile Gln
                500                 505                 510

Leu Phe Leu Gly Pro Lys Tyr Asp Ala Leu Gly Asn Leu Leu Asp Phe
            515                 520                 525

Ser Glu Ser Tyr Lys Asp Phe Tyr Glu Ile Asp Tyr Trp Ile Thr Asp
    530                 535                 540

Val Asn Ala Gly Leu Asn Lys Leu Glu Arg Thr Ser His Asp Phe Ile
545                 550                 555                 560

Phe Leu Met Ala Asp Arg Asp Pro Ser Glu Ile Leu Tyr Lys Arg Val
                565                 570                 575

Leu Lys Ala Leu Asp Gly Ser Glu Lys Phe Met Tyr Lys Lys Asn Leu
            580                 585                 590

Tyr Gly Ile Pro Glu Arg Leu Leu Pro Lys Gly Lys Arg Ala Gly
        595                 600                 605

Ser Ile Phe Gln Leu Phe Ala Tyr Val Ser Pro Val Thr Gln Pro Val
    610                 615                 620

Thr Tyr Lys Ser Arg Val Phe Gly Ser Tyr Gln Tyr Met Lys Pro
625                 630                 635                 640

Gly Gly Phe Pro Leu Asp Arg Pro Ile Tyr Tyr Pro His Phe Gln Gly
                645                 650                 655

Pro Asn Met Phe Phe Lys Asp Ile Thr Ile Tyr His Lys Thr Asp Val
                660                 665                 670

Asp Pro Asn Ala Thr Thr
            675

(2) INFORMATION FOR SEQ ID NO: 6:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 6:

ARYTGRAANA CYTTYTTYTG                                                    20

(2) INFORMATION FOR SEQ ID NO: 7:

(i) SEQUENCE CHARACTERISTICS:
        (A) LENGTH: 20 base pairs
        (B) TYPE: nucleic acid
        (C) STRANDEDNESS: single
        (D) TOPOLOGY: linear
```

(xi) SEQUENCE DESCRIPTION: SEQ ID NO: 7:

GAYTTYTAYT AYACNGAYGT                                                20

(2) INFORMATION FOR SEQ ID NO: 8:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO: 8:

GGAAATCTTG ATCAGCTATC AC                                             22

(2) INFORMATION FOR SEQ ID NO: 9:

(i) SEQUENCE CHARACTERISTICS:
        (A) LENGTH: 31 amino acids
        (B) TYPE: amino acid
        (C) STRANDEDNESS: single
        (D) TOPOLOGY: linear (xi) SEQUENCE DESCRIPTION: SEQ ID NO: 9:

```
Thr Asp Phe Tyr Tyr Thr Asp Val Ile Ala Asp Gln Asp Phe Leu Leu
1               5                   10                  15
Lys Gln Lys Lys Val Phe Gln Leu Leu Tyr His Val Ser Gln Pro
            20                  25                  30
```

(2) INFORMATION FOR SEQ ID NO: 10:

(i) SEQUENCE CHARACTERISTICS:
        (A) LENGTH: 93 base pairs
        (B) TYPE: nucleic acid
        (C) STRANDEDNESS: single
        (D) TOPOLOGY: linear (xi) SEQUENCE DESCRIPTION: SEQ ID NO: 10:

ACNGAYTTYT AYTAYACNGA YGTNATHGCN GAYCARGAYT TYYTNYTNAA RCARAARAAR    60

GTNTTYCARY TNYTNTAYCA YGTNWSNCAR CCN                                 93

(2) INFORMATION FOR SEQ ID NO: 11:

(i) SEQUENCE CHARACTERISTICS:
        (A) LENGTH: 68 base pairs
        (B) TYPE: nucleic acid
        (C) STRANDEDNESS: single
        (D) TOPOLOGY: linear (xi) SEQUENCE DESCRIPTION: SEQ ID NO: 11:

GATTTTTATT ATACTGATGT GATAGCTGAT CAAGATTTCC TTTTAAAGCA AAAGAAGGTT    60

TTTCAATT                                                             68

(2) INFORMATION FOR SEQ ID NO: 12:

(i) SEQUENCE CHARACTERISTICS:
        (A) LENGTH: 68 base pairs
        (B) TYPE: nucleic acid
        (C) STRANDEDNESS: single
        (D) TOPOLOGY: linear (xi) SEQUENCE DESCRIPTION: SEQ ID NO: 12:

GACTTTTATT ACACTGACGT GATAGCTGAT CAAGATTTCC TTTTAAAGCA AAAAAAGGTA    60

TTTCAACT                                                             68

-continued

```
(2) INFORMATION FOR SEQ ID NO: 13:

(i) SEQUENCE CHARACTERISTICS:
          (A) LENGTH: 68 base pairs
          (B) TYPE: nucleic acid
          (C) STRANDEDNESS: single
          (D) TOPOLOGY: linear (xi) SEQUENCE DESCRIPTION: SEQ ID NO: 13:

GATTTTTATT ATACTGATGT GATAGCTGAT CAAGATTTCC TTTTAAAGCA AAAGAAGGTA      60

TTTCAACT                                                               68
```

INSECTICIDAL TOXINS FROM THE PARASITIC WASP *BRACON HEBETER*

This is a Continuation of application Ser. No. 08/288,408, filed on Aug. 10,1994, now U.S. Pat. No. 5,554,592, which is a Continuation of application Ser. No. 08/013/890, filed Feb. 5, 1993, now abandoned, which is a Continuation-In-Part of application Ser. No. 07/897,192, filed Jun. 10, 1992, now abandoned, which is a Continuation-In-Part of application Ser. No. 07/847,570, filed Mar. 4, 1992, now abandoned.

This invention is directed to toxins active against insects which are isolated from the parasitic wasp Bracon hebetor, the nucleic acids which encode the toxins, cloning of the toxins, use of the toxins to control insects, and genetically engineered virus vectors carrying the toxin gene.

BACKGROUND OF THE INVENTION

In recent years, venoms of insects and arachnids, in particular spiders and scorpions, have been investigated as a potential source of biologically active substances for use in various fields such as medicine and agriculture. Examples of such work include:

EP Patent Application, Publ. No. 208 523 A2: Glutamate Antagonists Isolated from New World Spiders Argiope trifasciata and Araneus gemma.

EP Patent Application, Publ No. 156 540: Glutamate Receptor Inhibitor obtained from Nephila clavata.

Grishin et al., 1986. "Ion Channel Blocker from the Venom of Argiope lobata" *Biorg. Khim.* 12(8):1121–1124.

Usherwood et al., 1984. "Glutamate Channel Blockade by Venoms of Argiope trifasciata and Araneus gemma" *J. Physiol. Paris* 79:241–245.

Aramaki et al. 1986. "Glutamate Potential Suppressor from Nephila clavata and Nephila maculate" *Proc. Japan Acad.* 62, Ser B:359–362.

Usherwood et al., 1985. "Antagonism of Glutamate Receptor Channel Complexes by Spider Venom Polypeptides" *Neurotoxicology* 6(2):239–250.

Adams et al. 1986. "Synaptic Toxins from Agelenopsis aptera" *Insect Neurophysiology*, Borkovec et al., Eds. Humana Press, Clifton, N.J. 397–408.

Bracon hebetor (also known as Habrobracon hebetor and Microbracon hebetor) is a small (ca. 2 mm, less than 1 mg) ectoparasitic wasp, which has a venom that is paralytic to lepidopterans (Drenth, D. 1974, Toxicon 12:189–192). The quest to identify toxins in B. hebetor venom has continued for several years (see, e.g. Visser et al, 1976, Toxicon 14:357–307; Visser et al, 1983, Comp. Biochem. Physiol. 75B:523–530; and Spanjer et al, 1977, Toxicon 15:413–421). Most attempts have been frustrated by the lability of the toxins. Two protein toxins (mol. wt. 44 and 57 kda) have been purified and partially characterized, but they represent only 2% of the original insecticidal activity (Visser et al, supra, 1983). More recently, Slavnova et al, 1987 *Doklady Akademii Nauk USSR* 297:492–494 reports isolation of a toxin having a mass of 18 kda.

DESCRIPTION OF THE INVENTION

It has now been found that certain polypeptides, when isolated from the venom of the wasp Bracon hebetor are toxic, i.e. paralytic and/or lethal to insects, particularly of the order Lepidoptera, at surprisingly low concentrations.

The present invention, therefore, concerns toxins free from associated wasp polypeptides which demonstrate toxicity towards insects. These polypeptides may be isolated from, or be constructed to show substantial sequence homology to polypeptides isolated from the venom of Bracon hebetor. Preferred peptides are rather large, and may be characterized in having a molecular weight which exceeds 70,000 da. Five preferred polypeptides were isolated and were designated Brh-I to Brh-V.

As used throughout the specification and claims, the following definitions are intended:

Associated wasp polypeptides—polypeptides naturally occurring in the venom of B. hebetor which are toxic to insects.

Homologous polypeptide—a polypeptide which is identical to one of the native toxins of this invention, or substantially homologous (at least 80%) with respect to the amino acid sequence, such that it demonstrates substantially the same insect toxicity in in vivo assays as a native toxin.

Homologous nucleotide sequence—a sequence which will hybridize to the reference sequence under stringent hybridization conditions.

Stringent hybridization conditions—those in which hybridization is effected in a standard manner at 65° C. in 4X buffered saline (a.k.a. SSPE buffer) followed by merely washing at 52° C. in 0.2 X SSPE, which will not affect true hybrids which have formed.

Figure 1:
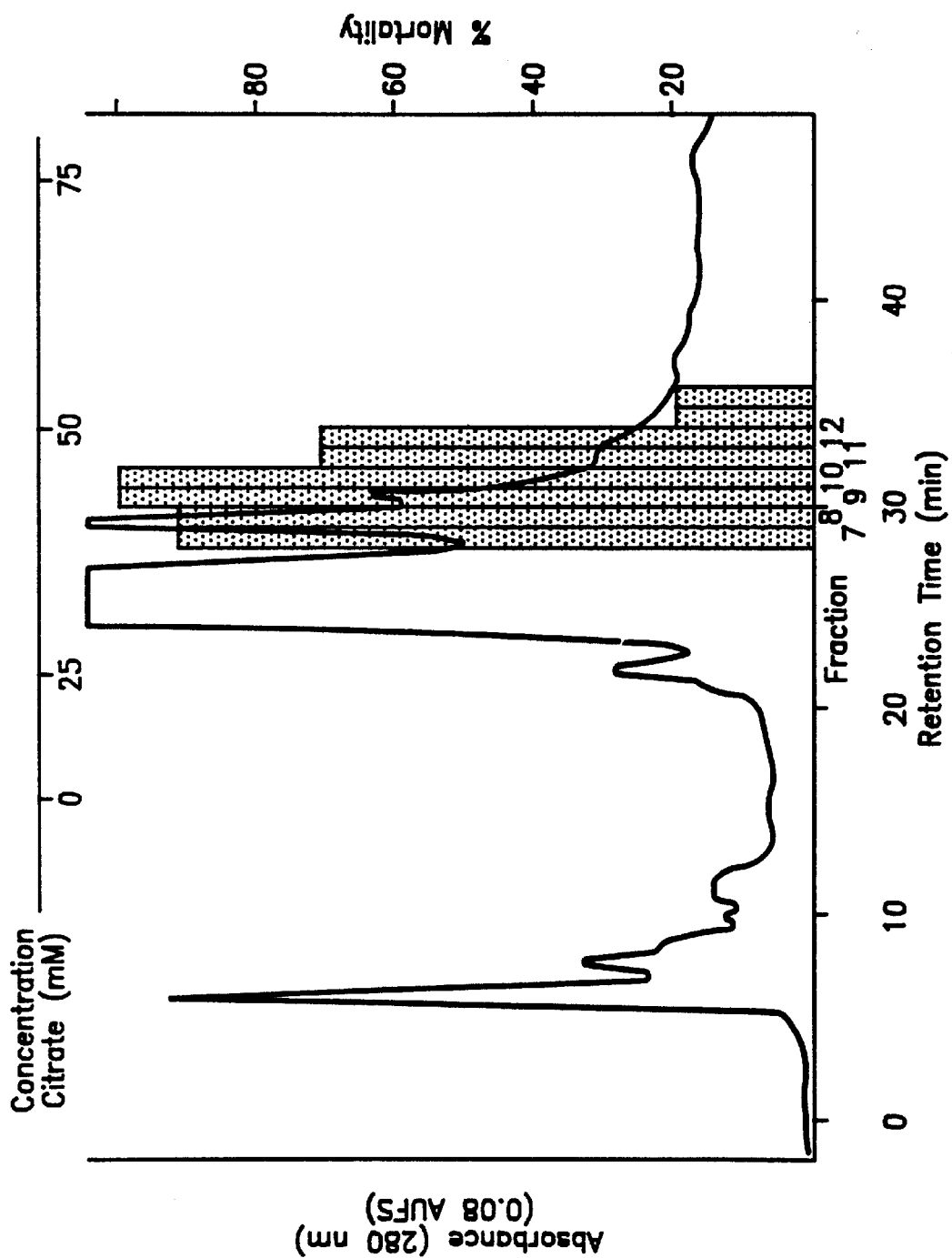
FIG. 1 demonstrates the purification of toxins from 300 B. hebetor venom glands using anion-exchange chromatography.

The toxins of this invention are quite labile under many isolation conditions. As they are particularly unstable at low pH, reverse-phase HPLC was contraindicated. The successful structure elucidation of toxins which are part of this invention is predicated on the purification by anion-exchange chromatography which was monitored by reversed-phase HPLC. The results of the anion-exchange chromatography are shown in FIG. 1. Various fractions, designated Fractions 7–13 are identified, and their insect mortality is assessed.

Figure 2:
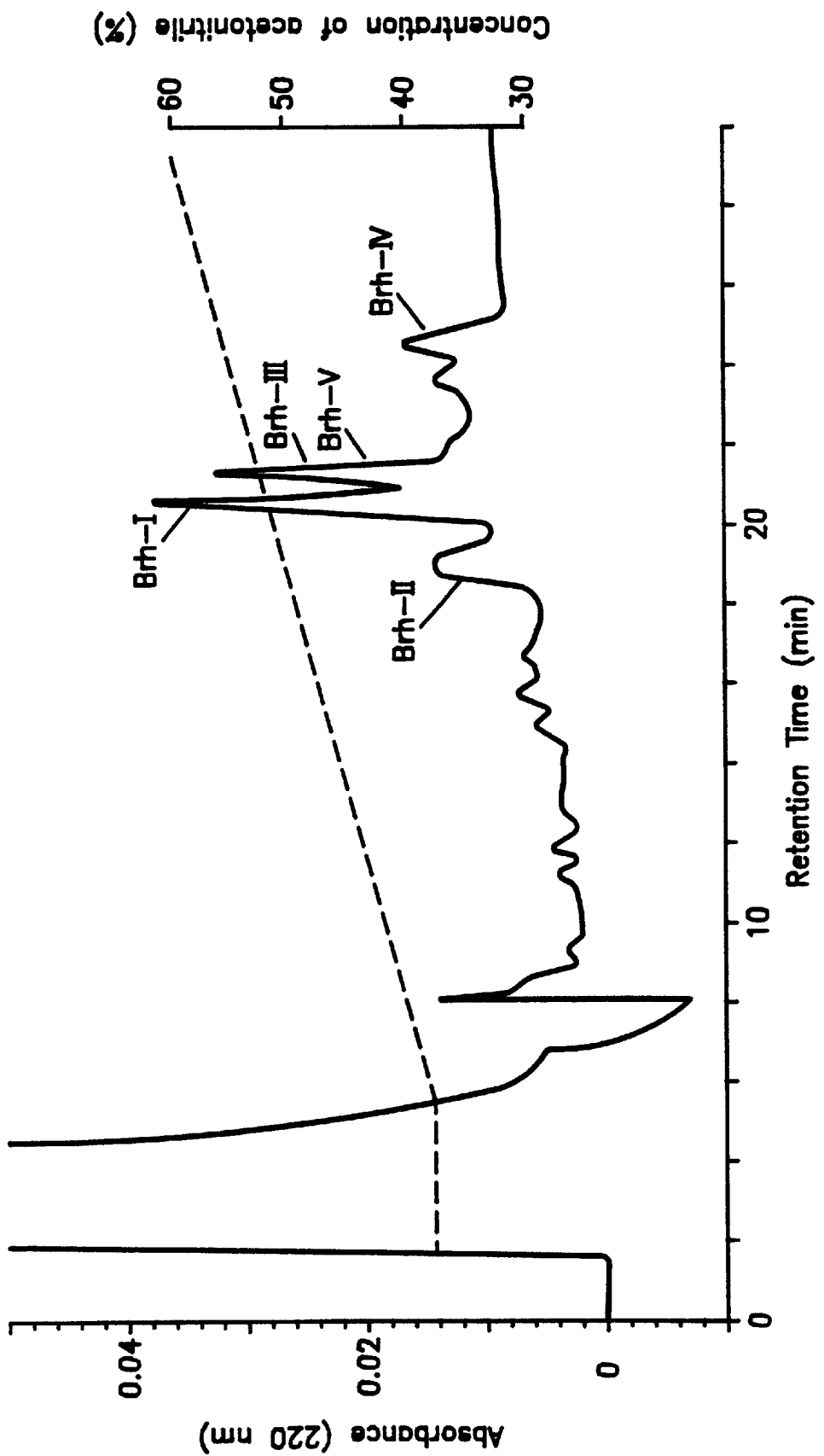
FIG. 2 is the reversed-phase HPLC analysis of combined fractions 7–13 from FIG. 1, using 25 gland-equivalents.
Figure 3:
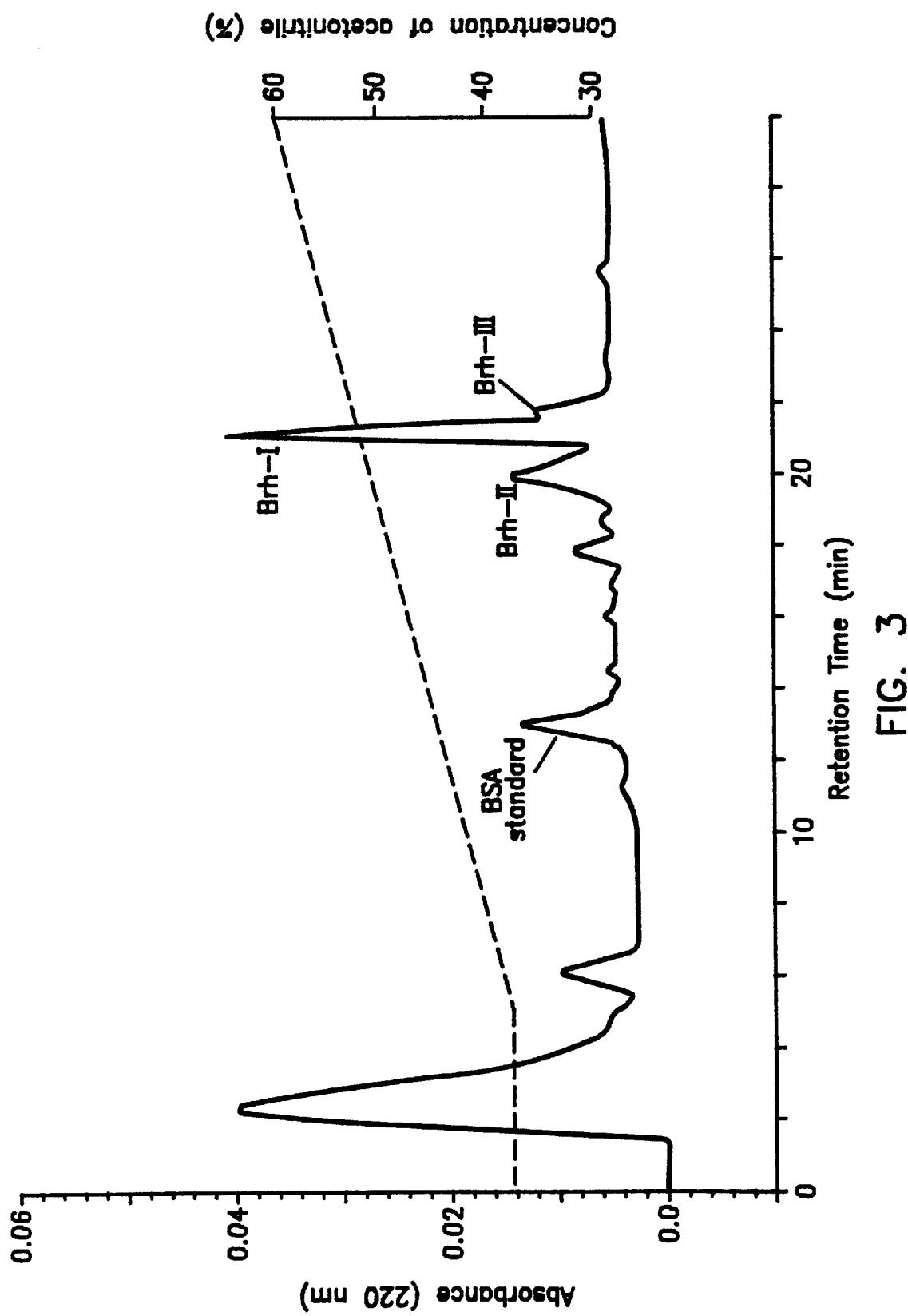
FIG. 3 is the reversed-phase HPLC analysis of Fraction 8 from FIG. 1 (25 gland equivalents). This is predominantly Brh-I.
Figure 4:
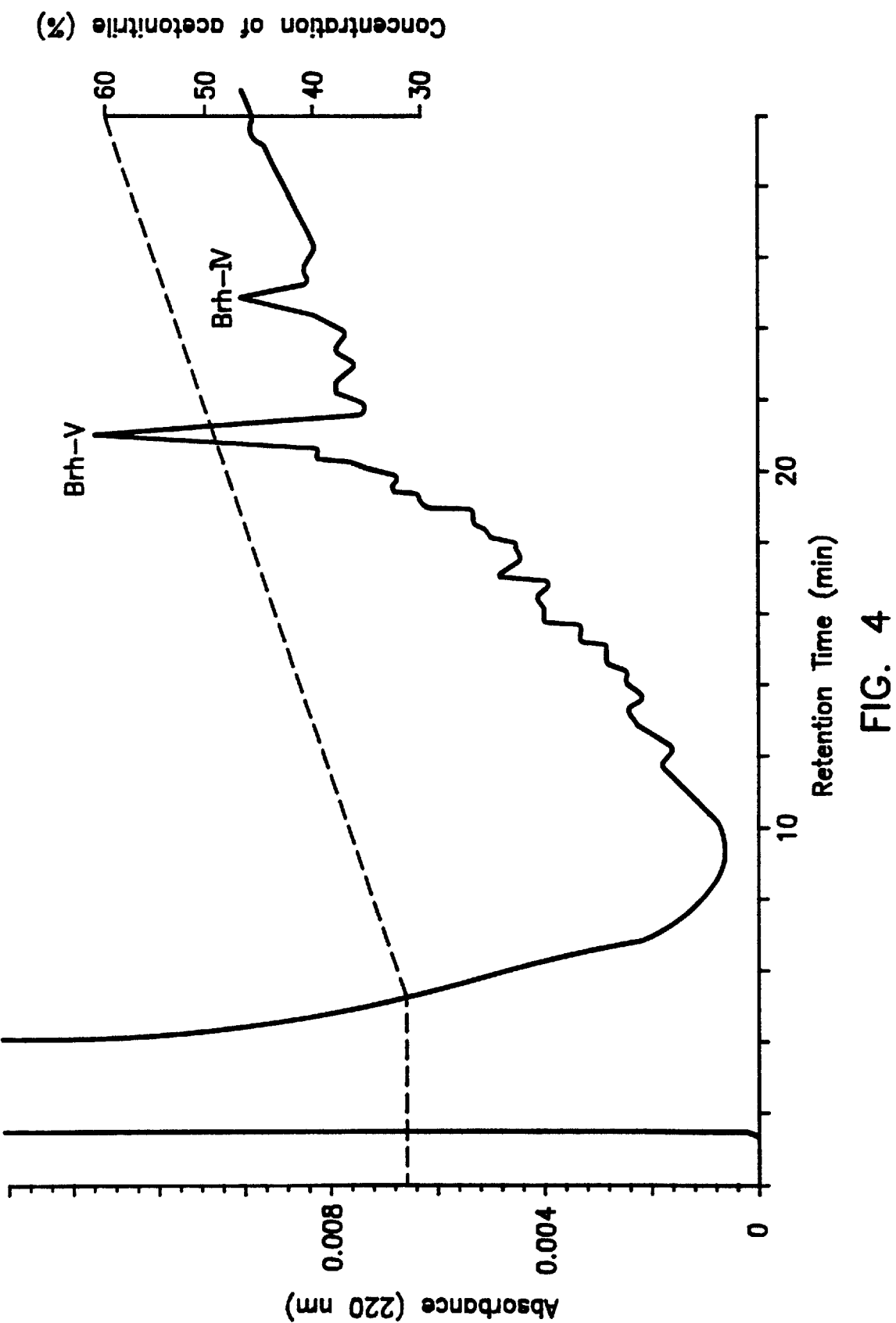
FIG. 4 is the reversed-phase HPLC analysis of Fraction 11 from FIG. 1 (25 gland equivalents). This is predominantly Brh-V.

As ultraviolet absorbance was of limited utility during toxin purification by ion-exchange, short (1 min) fractions were collected relative to contaminant absorbance (280 nm) and each fraction was assayed for bioactivity and purity (typically 25 gland equivalents using reverse-phase HPLC). Results are illustrated in FIGS. 2, 3, and 4.

In order to consistently recover toxins exhibiting high bioactivity, it was necessary to add a protein carrier (bovine serum albumin) prior to desalting by membrane filtration. Purified toxins could not be freeze-dried, even in the presence of BSA and were best stored in a solution (0.02M ammonium carbonate, pH 9.2, 4° C). Under these conditions, the toxins were stable for at least two weeks.

Thus one aspect of this invention is a polypeptide free from associated wasp polypeptides substantially homologous to a polypeptide isolated from Bracon hebetor and exhibiting insect toxicity. Preferred polypeptides have a molecular weight of at least 70,000 da. Examples of prefered polypeptides of this invention include: Brh-I, Brh-II, Brh-III, Brh-IV and Brh-V.

The preferred polypeptides of this invention may be characterized by their behavior during Anion-Exchange and Reversed-Phase HPLC as follows, the complete conditions of which are given in Example 1. By following the procedures set forth in Example 1, ie. Anion-Exchange chromatography followed by Reversed-Phase chromatography, peaks characteristic of Brh-I, Brh-II, Brh-III, Brh-IV, and Brh-V can be identified.

Three of the five native toxins were sequenced at least partially. Results are presented below.

(produced) in an amount sufficient to enhance the virus insecticidal effect on the insect. Such a recombinantly modified baculovirus DNA may also be used as a vector for the introduction of the wasp toxin-producing gene into cells, particularly insect cells, to provide further systems for the production of toxins.

A number of baculoviruses are suitable for use as vectors, and are known in the art, such as the nuclear polyhedrosis virus from *Autographa californica, Heliothis virescens,* and *Bombyx mori.* Suitable techniques are described, for example in European Patent Application 0175 852 and U.S. Pat. No. 4,745,051, both of which are hereby incorporated by reference.

Thus, other aspects of this invention are nucleic acids sequences (RNAs and DNAs) comprising those which encode toxin polypeptides and nucleic acid sequences which are substantially homologous to a native sequence. The nucleic acid sequences of this invention may also include sequences which are not expressed in the final polypeptide product, such as signal sequences, termination sequences, and the like.

TABLE 1

```
             1         5              10             15             20         25
Brh-I        T  D  F  Y  Y  T  D  V  I  A  D  Q  D  F  L  L  K  Q  K  K  V  F  Q  L
Brh-V        H  V  Q  T  Y  T  A  D  M  D  F  K  H  K  Q  K  K  I  Y  H  L  F  -  -
Brh-III      L  F  D  F  I  V  H  A  K  D  I  L  G  G  I  D  N  L  A  K  G  I  -  I/Q 30             35             40
Brh-I        L  Y  H  V  S  Q  P  -  I  S  N  -  -  -  F  Q  -  -  L  K        (SEQ. ID. NO.: 1)
   Brh-V              -  -  Q                                                   (SEQ. ID. NO.: 2)
Brh-III      A  I  N  K  V  -  -  V  I  -  K  V  Q  -  Q  A                    (SEQ. ID. NO.: 3)
```

The polypeptides of this invention may be prepared by a variety of techniques. They may, for example, be isolated from the crude venom of B. hebetor using purification techniques, such as those presented in the Examples. Alternatively, with knowledge of the amino acid sequence of the polypeptides, synthetic construction, using conventional protein synthesis techniques may be employed.

A further technique which may advantageously employed in the production of polypeptides of this invention involves the construction, by conventional methods, of a DNA sequence which, upon expression, encodes a polypeptide according to this invention. Such DNA sequences may then be inserted into an appropriate vector, either alone or in combination with other homologous or heterologous DNA sequences whose function may be to control the expression of the polypeptide-encoding DNA sequence of interest or may result in, for example, a fusion protein, enhancing or extending the activity of the toxin DNA expression product therefrom. Suitably employed as vectors are plasmids, phages, and viruses, the use of which for such purpose is common knowledge to the ordinary artisan. Cells in which a vector containing such a toxin DNA may be expressed, include, for example, prokaryotic cells such as *E. coli*, and *Bacillus* spp., or eukaryotic cells such as yeast cells or insect cells.

A preferred method for producing the toxin polypeptides directly as a toxic product such that no work-up towards isolation, purification, and formulation of an expression product is required is by employing an insect specific virus (baculovirus) as a vector. A gene encoding the desired polypeptide toxin is inserted into the baculovirus DNA, and is under the control of a baculovirus promoter. After the recombinant hybrid baculovirus is ingested by the insect, the virus multiplies inside the insect and the toxin is expressed A further aspect of this invention, therefore involves the cloning and genetic engineering of genes encoding the various toxins, and in particular Brh-I. While Brh-I is presented as an Example, any of the polypeptides of this invention may be similarly sequenced and cloned.

Starting with approximately 3.1 g of wasps, approximately 8 µg of poly A+ mRNA was obtained using the procedures detailed in the Examples. Degenerate oligonucleotide primers corresponding to two regions of the nucleotide sequence obtained by reverse translation of the mature Brh-I peptide were synthesized and used for PCR amplification from B. hebetor mRNA. DNA fragments with the expected size of approximately 130 bp were produced in the PCR reaction. The DNA fragments were gel purified, cloned into pTZ18R, and three clones were sequenced. All three of these clones contained a reading frame that matched a portion of the amino acid sequence of mature Brh-I toxin. A nondegenerate primer designed to match a region from within the amplified sequence was end-labelled with $^{32}$p and used to screen a λZAPII cDNA library made from B. hebetor. Three positive plaques were detected in a library screening of approximately $1.2 \times 10^6$ plaques.

After plaque purification and in vivo excision of the cDNA containing pBluescript SK- plasmids from the λZAPII clones, the cDNA inserts of 3 clones were subjected to DNA sequence analysis. In order to determine the expected size of a full length cDNA, a primer extension reaction was performed with B. hebetor mRNA. The nucleic acid and amino acid sequence of Brh-I is given in TABLE 2 (SEQ. ID. NO.: 4 and SEQ. ID. NO.: 5). Translational initiation very likely occurs at the ATG as indicated in TABLE 2 because a) this is the first methionine codon encountered in the cDNA; b) the codon for methionine is found in the sequence ATAAMTGC, which conforms with the ribosome initiation site consensus sequence determined by Kozak, M., 1989, *J. Cell Biol.* 108:229–241; and c) there is a translational stop sequence, TAA, in frame with the Brh-I open reading frame just upstream from this methionine codon. The predicted translation product for the cDNA is a molecule of 678 amino acids. The amino acid sequence given in TABLE 2 has an 18 amino acid sequence at the N-terminus preceding the sequence determined by analysis of the isolated polypeptide (Table 1). As this 18 amino acid sequence has many of the properties expected for a signal sequence (see, e.g., von Heijne, G. *Nucl. Acids Res.* 14:4683–4690) it appears that this sequence is a signal sequence which is cleaved after translation.

The molecular weight of mature Brh-I predicted from the cDNA sequence is 77,912. This is somewhat larger than the value determined by SDS-PAGE analysis of isolated Brh-I (approximately 73,000), however, the amino acid composition determined for Brh-I and for the cDNA translation product agree within experimental error, suggesting that no other extensive proteolytic processing occurs besides signal sequence cleavage.

Because of the very high level of paralytic activity that Brh-I elicits upon injection of a number of different insects, cDNAs encoding Brh-I toxin may be cloned in an insect baculovirus. Upon expression in the insect, there will be a quicker cessation of feeding than occurs after infection with wild type baculoviruses. Insect baculoviruses occur in two forms, occluded viruses, which are responsible for the spread of viruses between insects, and nonoccluded or budded viruses which are responsible for the cell to cell spread of viruses within an infected insect. Infection of insects per os normally requires the occluded form of the virus. Thus a further aspect of this invention is a recombinant virus containing a gene encoding a toxin of this invention inserted at a locus such that occlusion body formation is not disrupted. One such locus is the p10 locus.

Polypeptides isolated from or those showing substantial homology to those isolated from the venom of *B. hebetor* are useful as insect toxic agents. In particular, they are useful toxic agents against insects of the order Lepidoptera, for example, *Heliothis virescens, Autographa californica*, and the insects of the genus Spodoptera. Both the purified toxin and viruses transformed to produce the toxin are assayed for bioactivity on larvae including: tobacco hornworms (*Manduca sexta*), tobacco budworms (*Heliothis virescens*) and beet armyworm (*Spodoptera exigua*). Toxicity is demonstrated by the ability of the polypeptides to cause paralysis and/or death of the test larvae.

The present invention also provides the use of polypeptides isolated from, or polypeptides showing substantial sequence homology to those isolated from *Bracon hebetor* as insect toxic agents. For use as insecticides, the recombinant viruses which produce polypeptides of the invention may be combined with suitable carrier substances such as those typically found in insect control formulations, such as adjuvants, diluents, modifiers or conditioning agents. The formulations may be in the form of solutions, emulsions, dispersions, powders, dusts, granules and the like. It may be advantageous to include a surface active agent such as DMSO in the formulation so that the toxin passes directly through the cuticle of the insect and avoids the digestive enzymes which might affect its activity.

These compositions are advantageously applied to the insect or its locale in an amount suitable to control the target insects. By control, as used herein, is meant the induction of paralysis, mortality, or cessation of eating. Dosages of the composition of the invention will depend on numerous factors, including the pest to be controlled and the climatic conditions, but will generally be in the range of 0.5 to 100 kg/hectare, preferably 10–50 kg/hectare.

The following non-limiting Examples are presented to better illustrate the invention.

EXAMPLE 1

Isolation of Toxins

*B. hebetor* adult wasps are purchased from Biofac, Inc., Mathis Tex. Upon arrival, wasps are frozen at −20° C. until used. Venom glands and associated tissue are removed from female wasps and are stored in 1.5 ml polypropylene tubes at −20° C. until processed.

Purification. Lots of 100 venom glands are homogenized manually with a glass pestle in 1 ml water. After centrifugation at 3000×g, the supernatants from 300 glands are passed through Bio-Rad 10 DG size-exclusion columns. The excluded fraction (mol. wt >6 kda) is purified by ion-exchange chromatography.

Anion-exchange chromatography is performed with a Perkin-Elmer pump (410 BIO), a Spectra-Physics ultraviolet detector (Model 8300, 280 nm) and an Altex column (Spherogel-TSK, DEAE-5PW, 7.5×75 mm) with a elution at 1 ml/min. The elution solvent is citrate in 0.02M ammonium carbonate containing 10% aceto-nitrile, pH 8.2: 0 mM citrate for 15 min, linear gradient to 25 mM over 5 min, and 25 to 75 mM over 50 min. Individual fractions are bioassayed using *M. sexta* larvae. As shown in FIG. 1, all insecticidal activity is found in one broad zone (Fractions 7–13). Collectively, these fractions contain several wasp toxins (See FIG. 2, 3 and 4), but only 59 µg total protein from 300 venom glands, representing an approximately 4000-fold purification of toxins based on initial whole wasp mass.

Reverse phase liquid chromatography (HPLC) is performed using a Hewett Packard (HP) pump (Model 1090), an HP diode array detector (Model 1040, 220 and 280 nm), and a narrow-bore Vydac $C_4$-300 A column (15×0.2 cm) with a flow rate of 0.3 ml/min. The eluent is acetonitrile in 0.1% trifluoroacetic acid: 35% for 5 min, linear gradient 35 to 60% over 25 min. HPLC demonstrates that most individual fractions from ion-exchange chromatography are mixtures of toxins. However, fractions 8 and 11 are sufficiently pure to allow further characterizations. Fraction 8 contains predominantly Brh-I while Fraction 11 contains mostly Brh-V (See FIGS. 3 and 4).

Figure 5:
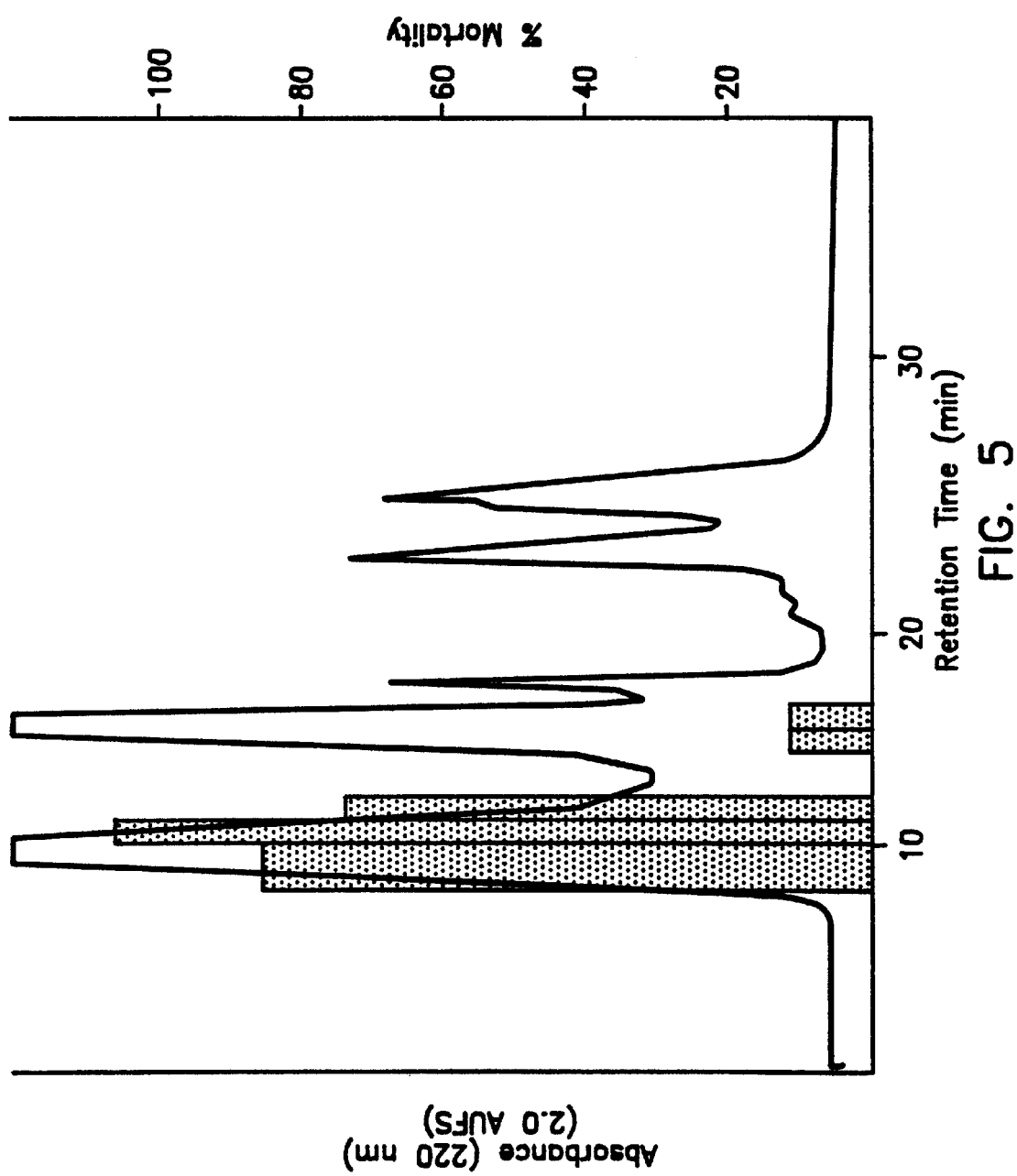
FIG. 5 is the size-exclusion HPLC analysis of toxins from 80 B. hebetor venom glands.

Size-exclusion chromatography employed the same Perkin-Elmer pump and Spectra-Physics detector as above with an Altex Spherogel-TSK 3000SW column (7.5×300 mm) with a flow of 0.5 ml/min. The eluent is 10% aceto-nitrile. Results are shown in FIG. 5.

EXAMPLE 2

Bioassay

The bioactivity of whole venom glands is determined for 50 glands homogenized in ice water. After centrifugation at 3000×g, 3 µl aliquots are injected into the pronotum of lepidopteran larvae which are scored for mortality at 24 hrs. The lethal dose for 50% of the treated larvae ($LD_{50}$) is calculated by Probit analysis from duplicate lots of glands, each of with at least four dose rates.

Purified Brh-I and Brh-V toxins are assayed similarly. Prior to the bioassay, 1 min. fraction from the ion-exchange purification are desalted using CentriconU/U-10 microconcentrators (Amicon). Bovine serum albumin (100 μg) is added to samples prior to desalting to improve recovery of toxins. Toxins are concentrated to approximately 150 μl in 0.02 M ammonium carbonate for bioassay.

The following larvae are bioassayed: *Manduca sexta* (tobacco hornworm) third stadium; *Heliothis virescens* (tobacco budworm) fourth stadium; *Helicoverpa zea* (corn earworm) fourth stadium; *Spodoptera exigua* (beet armyworm) fifth stadium; *Galleria mellonella* (wax moth) fourth stadium; *Trichoplusia ni* (cabbage looper) fifth stadium; *Pieris rapae* (cabbage butterfly) third stadium; and *Diabrotica undecimpunctata* (western spotted cucumber beetle) third stadium. Results are presented in Tables 3 and 4, below.

TABLE 3

Bioactivity of Venom Gland Extract

|   | mass of larva (mg) | $LD_{50}$ glands/larva | $LD_{50}$ glands/g |
|---|---|---|---|
| M. sexta | 47 | 0.036 | 0.77 |
| H. virescens | 48 | 0.080 | 1.7 |
| S. exigua | 50 | 0.065 | 1.3 |
| G. mellonella | 61 | 0.00046 | 0.0076 |
| H. zea | 41 | 0.038 | 0.95 |
| T. ni | 66 | 0.0014 | 0.021 |
| D. undecimpunctata | 13 | >0.2 | >13 |
| P. rapae | 56 | 0.000073 | 0.0013 |

TABLE 4

Injection Assay

|   | $LD_{50}$ (μg/g) Brh-I | $LD_{50}$ (μg/g) Brh-V |
|---|---|---|
| M. sexta | 0.05* | 0.04* |
| S. exigua | 0.033* | 0.051* |
| H. virescens | 0.18* | 0.26* |
| H. zea | 0.045* | 0.085 |
| G. mellonella | 0.0023* | 0.00011 |
| T. ni | 0.019 | 0.0038 |

*Duplicate toxin isolation for bioassay

EXAMPLE 3

Sequence Analysis 900 venom glands are processed as described above. Purified toxins (43–77 pmol) are sequenced twice using an Applied Biosystems Model 477A pulsed liquid phase protein sequencer. Released phenylthiohydantoin amino acids are analyzed using an on-line analyzer (Applied Biosystems Model 120A). Brh-I is also converted to a reduced, carboxymethylated derivative prior to sequencing as described in Skinner et al, 1989 *J. Biol. Chem.* 264:2150–2155, which is hereby incorporated by reference.

Toxins Brh-I and Brh-V are analyzed for constituent amino acids after hydrolysis in vacuo by vapor from 6M HCl/1% phenol at 110° C. for 20 hrs. Hydrolysates are analyzed using a Hewlett Packard AminoQuant amino acid analyzer.

EXAMPLE 4

Isolation of mRNA

B. *hebetor* wasps are stored at −80° C. 3.15 g of both male and female wasps are homogenized with a Polytron for 1 min in 20 ml RNA extraction buffer (4M guanidine isothiocyanate, 50 mM sodium citrate, pH 7.0, and 0.1M 2-mercaptoethanol). Following homogenization, 1 ml 15% Sarkosyl is added. The homogenate is centrifuged at 8,000 rpm for 10 min at 4° C. in a Sorvall HB-4 rotor, and the supernatants are decanted into clean tubes to remove insoluble debris. This is repeated once and the supernatant is layered over 3 ml of 5.7M CsCl in 0.01M EDTA, pH 8.0, and is centrifuged for 17 hours at 35,000 rpm in a Beckman Ti55 rotor. The pellet is resuspended in 15 ml of FastTrack Lysis Buffer (Invitrogen Corp) and the mRNA is then isolated following the protocol provided by Invitrogen Corp for their FastTrack mRNA isolation kit.

EXAMPLE 5

PCR Amplification

Single-stranded cDNA is synthesized from *B. hebetor* mRNA (0.5 μg) using M-MLV reverse transcriptase (GIBCO-Bethesda Research Laboratories) primed with a degenerate 20-mer oligonucleotide primer with the following sequence (SEQ. ID. NO.: 6)

5'-A[A,G][C,T]TG [A,G]AA[ACGT]AC[C,T]TT[C,T] TT[C,T]TG-3'

This primer is complementary to a sequence derived by reverse translation of the Brh-I toxin N-terminal amino acid sequence. Following the cDNA synthesis, the reactions are heated to 90° C. for 5 minutes, cooled to room temperature and ethanol precipitated. The cDNA reaction product is amplified in a 50 μl reaction with PCR geneAMP reagents (Perkin-Elmer Cetus Instruments), using 2 μM each of the above primer and a second degenerative primer with the following sequence (SEQ. ID. NO.: 7):

5'-GA [C,T]TT[C,T]TA[C,T]TA[C,T]AC[A,C,G,T]GA [C,T]GT-3'

This primer corresponds to a second portion of the reverse translation product of the Brh-I toxin N-terminal amino acid sequence. PCR conditions are as follows: 1 min at 94° C.; 2 min at 37° C.; slow ramping of the temperature over 3 min to 72° C.; 3 min at 72° C.; 10 sec extension of the 72° C. segment per cycle for 30 cycles; and a final cycle extension of 72° C. segment for 10 min. The products of the PCR reaction are electrophoresed on a 2% Agarose gel in TBE buffer (Sambrook et al, 1989 *Molecular Cloning: A Laboratory Manual, 2nd Ed.* Cold Spring Harbor Laboratory Press, Cold Spring Harbor, N.Y.). A gel slice expected to contain the approximately 70 bp product is removed, and the DNA is isolated using Geneclean (Bio101) reagents according to the manufacturer's instructions. The DNA is then reamplified using the same primers and the same PCR conditions as described above.

The DNA fragments are then gel-purified and cloned into pTZ18R (BIO-RAD Laboratories) and three clones are sequenced. All three clones match the Brh-I sequence from Table 1. A non-degenerate primer, designed to match a region from within the amplified sequence (See Table 5) is end-labeled with $^{32}$p and used to screen a λZAPII cDNA library made from *B. hebetor* mRNA. Three positive plaques are detected in a library screening of approximately $1.2 \times 10^6$ plaques. One of the Brh-I positive clones has an insert size of approximately 3.0 kb, and the other two each have inserts of approximately 2.3 kb.

TABLE 5

Reverse translation and PCR Amplification of Brh-I toxin mRNA.

Figure 6:
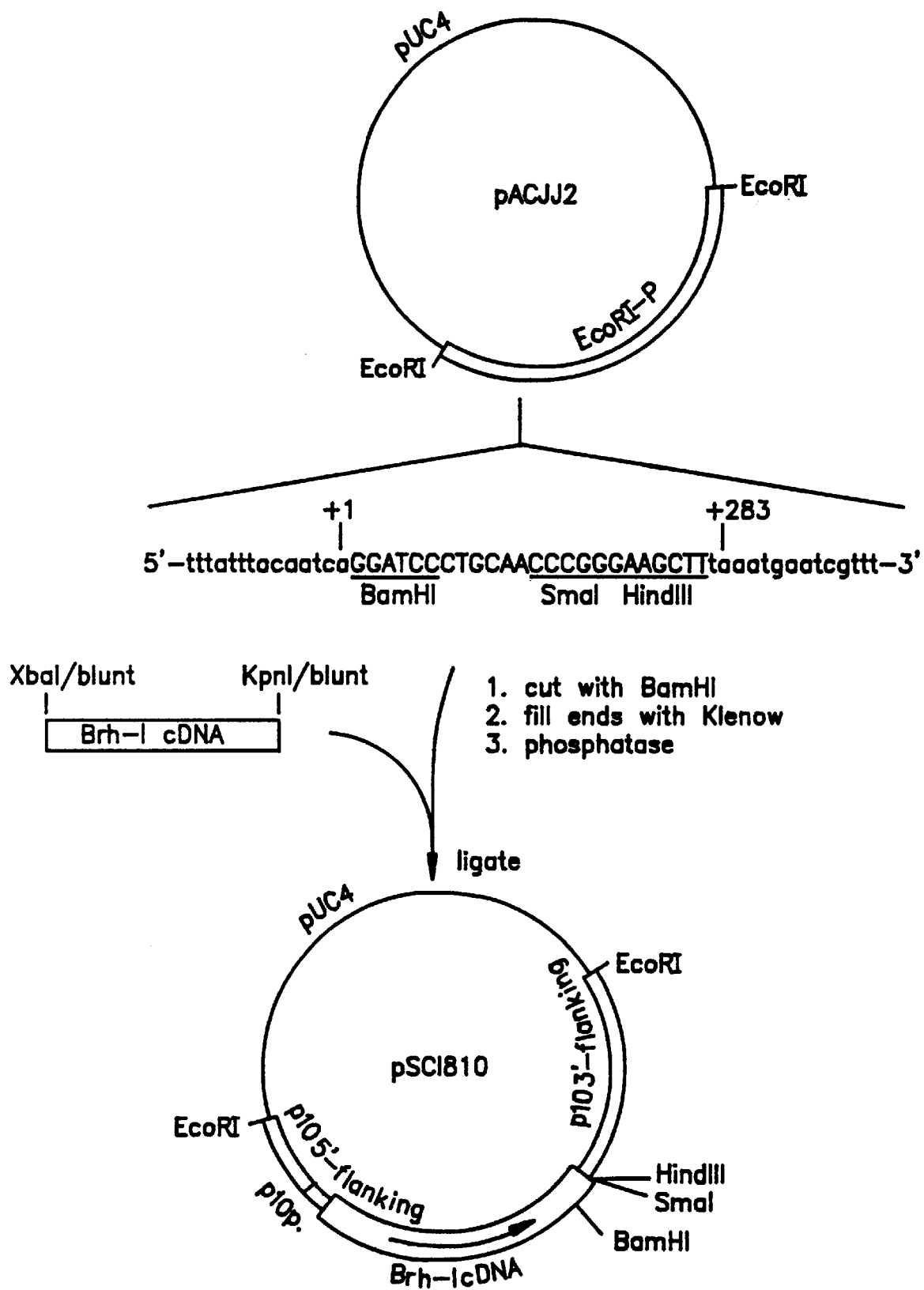
FIG. 6 is a diagram of plasmid pSCI810, containing the Brh-I gene.

The amino acid sequence of amino acids 2 through 32 from the N-terminus of Brh-I toxin is shown on line 1. The nucleotide sequence derived by reverse translation of the Brh-I amino acid sequence is shown below the amino acid sequence on line 2. All possible nucleotides at each position are indicated; Y— C or T; R— A or G; M— A or C; W— A or T; H— A, C, or T; N— A, C, T, or G. Degenerate oligonucleotides corresponding to the first underlined region and the complement of the second underlined region are used as PCR primers for amplification from Brh-I mRNA. Lines 3, 4, and 5 show the nucleotide sequence from three cloned PCR fragments. Underlined sequences correspond to primer regions. Line 6 shows the sequence of the nondegenerate oligonucleotide which was used as a hybridization probe for screening the B. hebetor cDNA library.

presence of all four dNPTs to make the ends blunt, and then the cDNA containing insert is gel isolated. The plasmid pACJJ2, (obtained from Dr. Just Vlak, Dept. of Virology, Agricultural Univ., Wageningen, The Netherlands) which has a polylinker in place of the complete p10 open reading frame, is cut with BamHI, the ends are filled, phosphatased with calf intestinal phosphatase, and then is ligated with the isolated Brh-I cDNA to form pSC1810, as shown in FIG. 6.

Next, pBluescript KS$^+$ and pBluescript SK$^+$ are each digested with KpnI and XholI, treated with Klenow in the presence of dNPT's to make the ends flush, and then religated to form pBluescript KS$^+\Delta$XK and pBluescript

```
                        5                    10                    15
1   Thr Asp Phe Tyr Tyr Thr Asp Val Ile Ala Asp Gln Asp Phe Leu Leu Lys Gln

2   ACN GAY TTY TAY TAY ACN GAY GTN ATH GCN GAY CAR GAY TTY YTN YTN AAR CAR

3       GAT TTT TAT TAT AGT GAT GTG ATA GCT GAT CAA GAT TTC CTT TTA AAG CAA

4       GAC TTT TAT TAC ACT GAC GTG ATA GCT GAT CAA GAT TTC CTT TTA AAG CAA

5       GAT TTT TAT TAT ACT GAT GTG ATA GCT GAT CAA GAT TTC CTT TTA AAG CAA 6                            3'-CAC TAT CGA CTA GTT CTA AAG G-5'              (SEQ. ID NO.: 8)

20                   25                    30
1   Lys Lys Val Phe Gln Leu Leu Tyr His Val Ser Gln Pro                       (SEQ. ID. NO.: 9)

2   AAR AAR GTN TTY CAR YTN YTN TAY CAY GTN WSN CAR CCN                       (SEQ. ID. NO.: 10)

3   AAG AAG GTT TTT CAA TT0                                                   (SEQ. ID. NO.: 11)

4   AAA AAG GTA TTT CAA CT0                                                   (SEQ. ID. NO.: 12)

5   AAG AAG GTA TTT CAA CT0                                                   (SEQ. ID. NO.: 13)
```

DNA sequencing and Sequence Analysis. Double stranded pBluescript SK-plasmid DNA containing cDNA inserts are generated from λZAPII cDNA clones following the in vivo excision procedure described in the λZAPII instruction manual. The 5'-termini of the cDNA inserts are then subjected to PCR amplification using the primer indicated in Table 5 coupled with M13 reverse primer. The PCR products from the 5'-termini of the 2.3 kb cDNA inserts have identical sequences and that from the 3.0 kb cDNA sequence is the same as those of the 2.3 kb cDNA except for being shorter by four nucleotides.

The two XhoI fragments from within the cDNA insert are subcloned into the pBluescriptSK+II vector, and unidirectional deletion series are generated from both ends of each clone. Both strands of the cDNA are sequenced in their entirety, and is given in Table 2 (SEQ. ID. NO. 4 and SEQ. ID. NO.: 5).

The nucleotide sequences and predicted protein sequences are analyzed with the IntelliGenetics suite of sequence analysis programs.

EXAMPLE 5

Construction of Vectors

A plasmid containing the Brh-I cDNA is liberated from a recombinant λZAPII isolate by in vivo excision. The plasmid is cut with XbaI and KpnI, treated with Klenow in the SK$^+\Delta$XK, respectively. Each of these plasmids is then digested with ScaI and SalI. The larger of the two fragments from the ScaI and SalI digested pBluescript KS$^+\Delta$XK and the smaller of the two fragments from the ScaI and SalI digested pBluescript SK$^+$XK are isolated and ligated together to form pSCI235. Another plasmid, pSCI839 is constructed by subcloning an approximately 3 kb SalI fragment containing an intact polyhedrin gene into pSCI234 to form pSCI839. The SalI fragment containing the polyhedrin gene in pSCI839 is isolated from pSCI275, which is a pWE15-based cosmid vector containing a large segment of AcNPV DNA (randomly cloned from AcNPV strain LI) that includes the polyhedrin gene.

Figure 7:
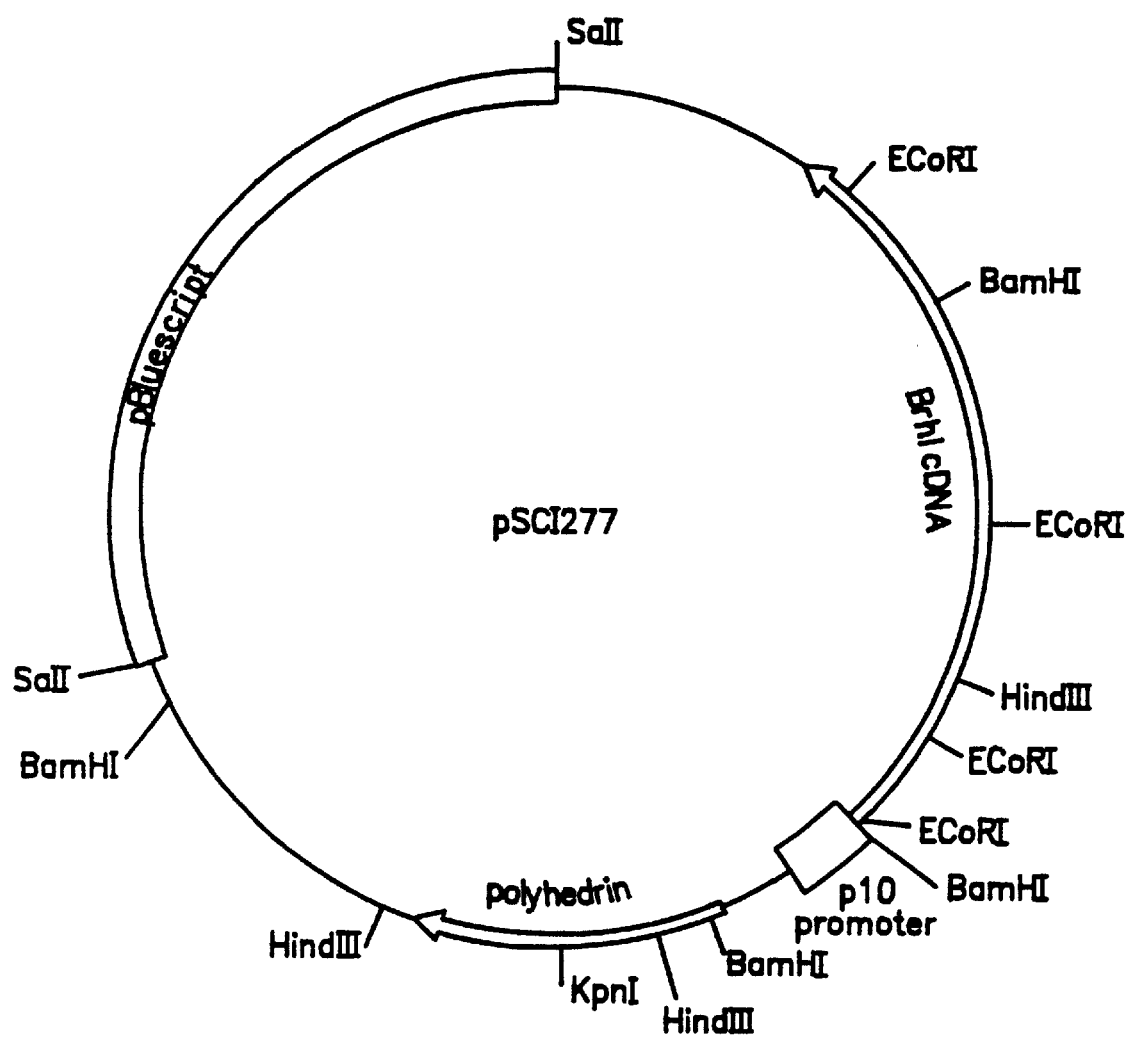
FIG. 7 is a diagram of plasmid pSCI277, containing the Brh-I gene linked to the p10 promoter.

Plasmid pSCI276 is formed by cutting pSCI810 with PstI and SpeI, making the ends blunt with T$_4$ DNA polymerase in the presence of dNTPs, and is religated. pSC1276 is then cut with SphI and SmaI, the SphI ends are made flush with T$_4$ DNA polymerase in the presence of dNTPs, and an approximately 2650 bp segment containing the Brh-I cDNA linked to the p10 promoter is isolated and cloned into the unique EcoRV site of pSCI839 to form pSC1277. The plasmid pSCI277 has a module containing the p10 promoter region linked to the Brh-I cDNA inserted at the EcoRV site just upstream of the intact polyhedrin gene; it is diagrammed in FIG. 7. After transfection of this plasmid with polyhedrin viral plasmid DNA, recombinant viruses are selected by their ability to form polyhedra$^+$plaques.

TABLE 2

BRH-I (SEQ. ID. NOS. 4 & 5)

```
GCAACACAAG TGTTACTTCG TTTGCCACTT CACTGTTGAA GAAAAATAAA AAATACATTT      60

TGATTATCAC TTGAATAATC TATA ATG CTG AAG AAG GTC TTT CTT TTG GCC        111
                           Met Leu Lys Lys Val Phe Leu Leu Ala
                            1                5

TCT TTG GCT ATT ATC GTG ATA AAA GCT G4T ACC GAT TTT TAT TAT ACA        159
Ser Leu Ala Ile Ile Val Ile Lys Ala Asp Thr Asp Phe Tyr Tyr Thr
 10              15                  20                  25

GAT GTG ATA GCT GAT CAA GAT TTC CTT TTA AAG CAA AAG AAA GTT TTT        207
Asp Val Ile Ala Asp Gln Asp Phe Leu Leu Lys Gln Lys Lys Val Phe
             30                  35                  40

CAA TTG TTG TAT CAT GTT TCA CAA CCA GAC ATC TCA AAT CCC GAG CTT        255
Gln Leu Leu Tyr His Val Ser Gln Pro Asp Ile Ser Asn Pro Glu Leu
             45                  50                  55

TTC CAG GAG GGA TTG GCT TAT GAC ATT GGA GCC AAT ATT GAT TCC TAT        303
Phe Cln Glu Gly Leu Ala Tyr Asp Ile Gly Ala Asn Ile Asp Ser Tyr
         60                  65                  70

TCT AAT AAG GAT GCA GTG AAT CAC TTC CTC GAG CTA TAC AAA TTC GGA        351
Ser Asn Lys Asp Ala Val Asn His Phe Leu Glu Leu Tyr Lys Phe Gly
 75                  80                  85

TTC CTT CCA AGA GGT GCA ATC TAC TCC CTC TAT TAT CCT AAA CTC TTG        399
Phe Leu Fro Arg Gly Ala Ile Tyr Ser Leu Tyr Tyr Pro Lys Leu Leu
 90                  95                 100                 105

GAC GAG ACT AAA GCC TTG TTC AAA TTG TTC TAC TAT GCC AAG GAC TTT        447
Asp Glu Thr Lys Ala Leu Phe Lys Leu Phe Tyr Tyr Ala Lys Asp Phe
             110                 115                 120

GAT ACT TTC TAT AAA ACT GCC CTT TGG GCG AGA AAT CGT TTG AAC GAA        495
Asp Thr Phe Tyr Lys Thr Ala Leu Trp Ala Arg Asn Arg Leu Asn Glu
             125                 130                 135

GGT GAA TTC ATA TGT GCC TTC TAT GAA GCT GTC ATC CGG CGT CCC GAC        543
Gly Glu Phe Ile Cys Ala Phe Tyr Glu Ala Val Ile Arg Arg Pro Asp
             140                 145                 150

ACA GAG TAT CTC CAG TTA CCG CCT TAT GAG TTA TAT CCC TAT GCG            591
Thr Glu Tyr Leu Gln Leu Pro Pro Tyr Glu Leu Tyr Pro Tyr Ala
         155                 160                 165

TTC TTC AAC AGT GAG GTA ATC GAG GCT GCA AAA AAT GCC AAA TTG TAC        639
Phe Phe Asn Ser Glu Val Ile Glu Ala Ala Lys Asn Ala Lys Leu Tyr
170                 175                 180                 185

AAT AAG CTT GTT GAA GGA AAT TCC TAC ATT ATC TAT GTC AAT TAC TCC        687
Asn Lys Leu Val Glu Gly Asn Ser Tyr Ile Ile Tyr Val Asn Tyr Ser
             190                 195                 200

GGC TGG TAC TTG AAT CGA GCT TAT GAT ACA GAG ATG AGA GTC AAC TAT        735
Gly Trp Tyr Leu Asn Arg Ala Tyr Asp Thr Glu Met Arg Val Asn Tyr
             205                 210                 215

TTC CTC GAA GAT ATC GGT TTA AAC ACC TTC TAC TTT TTC TAC CGC ATG        783
Phe Leu Glu Asp Ile Gly Leu Asn Thr Phe Tyr Phe Phe Tyr Arg Met
             220                 225                 230

GAT AAT CCA TTT TGG TTG AGC AGT GAG GAA TTT GGT TTG CAG AAA AAT        831
Asp Asn Pro Phe Trp Leu Ser Ser Glu Glu Phe Gly Leu Gln Lys Asn
         235                 240                 245

TTG CGT GGT GAG GAA TTT CTC TAT GTT CAC AAA ACA CTC TTG AAT CGT        879
Leu Arg Gly Glu Glu Phe Leu Tyr Val His Lys Thr Leu Leu Asn Arg
250                 255                 260                 265

TAC AAT TTG GAA AGA TTG GCA AAT GGC TTG GAG AAA ATT GAA GAA TTC        927
Tyr Asn Leu Glu Arg Leu Ala Asn Gly Leu Glu Lys Ile Glu Glu Phe
             270                 275                 280

CTT TGG GAG GGA GAA TTT TAT CCA GGC TAT TAT CCA ACT ATG GTC TAT        975
Leu Trp Glu Gly Glu Phe Tyr Pro Gly Tyr Tyr Pro Thr Met Val Tyr
             285                 290                 295
```

TABLE 2-continued

BRH-I (SEQ. ID. NOS. 4 & 5)

```
GGC AAT GGG CTG GCT TAT CCT CAG CGT CCA GGA ATG AGT AGG ATT CCT    1023
Gly Asn Gly Leu Ala Tyr Pro Gln Arg Pro Gly Met Ser Arg Ile Pro
        300                 305                 310

CCA TAT AAG TAT CAT TAT TTA CGG TAT ATC CAC GAT ATC GAA GAT AGA    1071
Pro Tyr Lys Tyr His Tyr Leu Arg Tyr Ile His Asp Ile Glu Asp Arg
        315                 320                 325

ATT TCA ACA GCC ATT GAC TTG GGC TAT ATA ATC GAC AGC GAT GGT AGT    1119
Ile Ser Thr Ala Ile Asp Leu Gly Tyr Ile Ile Asp Ser Asp Gly Ser
330                 335                 340                 345

CAC CAC AAC ATC TCA AGT GCG GAA GGA CTT AAG CTC TTA GGT AAC ATC    1167
His His Asn Ile Ser Ser Pro Glu Gly Leu Asn Leu Leu Gly Asn Ile
            350                 355                 360

ATC GAG GGT AAT GAA GAT AGT TGC AAT AAA AAC TTT TAT CAC AGC CTC    1215
Ile Glu Gly Asn Glu Asp Ser Cys Asn Lys Asn Phe Tyr His Ser Leu
                365                 370                 375

GAT TGG TAT GGT AGA AAG GTT CTT GGT TTC AAT CTC GAG CCC AAG ACT    1263
Asp Trp Tyr Gly Arg Lys Val Leu Gly Phe Asn Leu Glu Pro Lys Thr
            380                 385                 390

CCC TAT CAA GTT ATT CCA AGT GCA CTA GAG TCA TTT TCA ACT TGC ATG    1311
Pro Tyr Gln Val Ile Pro Ser Ala Leu Glu Ser Phe Ser Thr Cys Met
        395                 400                 405

AGA GAT CCG GCT TTC TAT CGT CTC TAC AAT AGA TAT CTG TCA TAC TGG    1359
Arg Asp Pro Ala Phe Tyr Arg Leu Tyr Asn Arg Tyr Leu Ser Tyr Trp
410                 415                 420                 425

TAC AGA TTC AAA GAA ACC TTG AAG CCA TAT TCT AAG AAT GAA ATA GTC    1407
Tyr Arg Phe Lys Glu Thr Leu Lys Pro Tyr Ser Lys Asn Glu Ile Val
                430                 435                 440

TTC TCT GAT TTG AAA TTT GAA TCA ATT GCT GTT GAT AAA TTG ATC ACA    1455
Phe Ser Asp Leu Lys Phe Glu Ser Ile Ala Val Asp Lys Leu Ile Thr
                445                 450                 455

TAT TTT GAT TAT TTT GAT TCA ACA ATT AGC AAT GGT CTA CCA ATT ACA    1503
Tyr Phe Asp Tyr Phe Asp Ser Thr Ile Ser Asn Gly Leu Pro Ile Thr
            460                 465                 470

AGT AAA CAA GAT GCT GAT AAT TTA ATG ATC AAA GTT CGC CAG AGT CGT    1551
Ser Lys Gln Asp Ala Asp Asn Leu Met Ile Lys Val Arg Gln Ser Arg
        475                 480                 485

TTA AAT AAT AAA CAC TTT ACC GTA CAT TTC GCC CTA AAT TCC GAT AAA    1599
Leu Asn Asn Lys His Phe Thr Val His Phe Ala Leu Asn Ser Asp Lys
490                 495                 500                 505

GCA CAA AAA GTT GCC ATT CAG CTG TTT CTT GGA CCC AAA TAT GAT GCA    1647
Ala Gln Lys Val Ala Ile Gln Leu Phe Leu Gly Pro Lys Tyr Asp Ala
                510                 515                 520

CTT GGT AAT TTA TTG GAC TTT TCC GAG AGT TAC AAA GAC TTT TAT GAG    1695
Leu Gly Asn Leu Leu Asp Phe Ser Glu Ser Tyr Lys Asp Phe Tyr Glu
            525                 530                 535

ATT GAC TAC TGG ATT ACT GAT GTG AAT GCT GGC TTG AAT AAA CTT GAA    1743
Ile Asp Tyr Trp Ile Thr Asp Val Asn Ala Gly Leu Asn Lys Leu Glu
            540                 545                 550

CGT ACC AGT CAC GAC TTT ATC TTT TTG ATG GCC GAC CGA GAT CCA AGT    1791
Arg Thr Ser His Asp Phe Ile Phe Leu Met Ala Asp Arg Asp Pro Ser
        555                 560                 565

GAA ATT TTA TAC AAA AGA GTT TTA AAG GCC CTT GAT GGA AGT GAA AAG    1839
Glu Ile Leu Tyr Lys Arg Val Leu Lys Ala Leu Asp Gly Ser Glu Lys
570                 575                 580                 585

TTC ATG TAC AAA AAG AAT TTG TAT CGC ATT CCG GAA CGT TTA CTT CTA    1887
Phe Met Tyr Lys Lys Asn Leu Tyr Gly Ile Pro Glu Arg Leu Leu Leu
                590                 595                 600
```

TABLE 2-continued
BRH-I (SEQ. ID. NOS. 4 & 5)

```
CCA AAA GGT AAA CGT GCC GGT AGT ATT TTC CAA CTG TTT GCC TAT GTA    1935
Pro Lys Gly Lys Arg Ala Gly Ser Ile Phe Gln Leu Phe Ala Tyr Val
            605                 610                 615

AGC CCA GTT ACC CAG CCA GTC ACC TAC AAA TCA CGA GTA TTT GGA TCT    1983
Ser Pro Val Thr Gln Pro Val Thr Tyr Lys Ser Arg Val Phe Gly Ser
            620                 625                 630

TAT CAA TAC TAC ATG AAA CCA GGT GGT TTT CCA CTG GAC AGG CCA ATC    2031
Tyr Gln Tyr Tyr Met Lys Pro Gly Gly Phe Pro Leu Asp Arg Pro Ile
            635                 640                 645

TAC TAT CCC CAT TTC CAA GGG CCC AAT ATG TTC TTC AAA GAT ATT ACG    2079
Tyr Tyr Pro His Phe Gln Gly Pro Asn Met Phe Phe Lys Asp Ile Thr
650                 655                 660                 665

ATT TAC CAC AAG ACT CAT GTG GAT CCT AAT GCT ACT ACC TAATTCCAAT     2128
Ile Tyr His Lys Thr Asp Val Asp Pro Asn Ala Thr Thr
                670                 675

TTTTTTACTC TATTTTCATT TGAGATTCTT ATCAAATTCA ATGTTTGTTT GTTAATATTG  2188

TCTTTGTAGA GCTTAGAATG TTAGATTGAA AATGTTTATT TCCATGACAA TTTATTATTT  2248

GTTATTGATA TTATCAATGA ATTCTCTGTC AGTCAACCTC AGAGAATATA AAATTTTATT  2308

ACAAAAATGT CGTATTGAGC ATAAATTCAT TATTTGGGAA AAATTTTCAA ATAAAAAGCA  2368

TATTTTCCAA CAAAAAAAA                                               2387
```

What is claimed is:

1. An isolated nucleic acid molecule encoding a polypeptide that exhibits insect toxicity, wherein the complement of said nucleic acid molecule hybridizes under stringent hybridization conditions to a nucleotide sequent that encodes SEQ ID NO:5.

2. An isolated nucleic acid molecule encoding a polypeptide that exhibits insect toxicity, wherein the complement of said nucleic acid molecule hybridizes under stringent hybridization conditions to nucleotides 85-2121 of SEQ ID NO:4.

3. An isolated nucleic acid molecule encoding a polypeptide that exhibits insect toxicity, wherein said polypeptide comprises SEQ ID NO:5.

4. An isolated nucleic acid molecule according to claim 3, comprising nucleotides 85-2121 of SEQ ID NO:4.

5. A baculovirus whose genome comprises a nucleic acid molecule according to claim 1.

6. A baculovirus whose genome comprises a nucleic acid molecule according to claim 2.

7. A method of controlling insects comprising infecting the insects with a baculovirus of claim 5.

8. A method of controlling insects comprising infecting the insects with a baculovirus of claim 4.

9. A baculovirus whose genome comprises a nucleic acid molecule according to claim 3.

10. A method of controlling insects comprising infecting the insects with a baculovirus of claim 9.

11. A baculovirus whose genome comprises a nucleic acid molecule according to claim 4.

12. A method of controlling insects comprising infecting the insects with a baculovirus of claim 11.

13. A vector comprising a nucleic acid molecule according to claim 11.

14. A vector comprising a nucleic acid molecule according to claim 2.

15. A vector comprising a nucleic acid molecule according to claim 3.

16. A vector comprising a nucleic acid molecule according to claim 4.

* * * * *